(12) United States Patent
Powell

(10) Patent No.: US 7,544,336 B2
(45) Date of Patent: Jun. 9, 2009

(54) STERILIZATION TRAY WITH BASE AND ELASTOMERIC LID

(76) Inventor: Andrew Powell, 32 Smada Dr., Sanford, ME (US) 04073

( * ) Notice: Subject to any disclaimer, the term of this patent is extended or adjusted under 35 U.S.C. 154(b) by 334 days.

(21) Appl. No.: 11/268,363

(22) Filed: Nov. 7, 2005

(65) Prior Publication Data

US 2007/0104609 A1    May 10, 2007

(51) Int. Cl.
A61L 2/06 (2006.01)

(52) U.S. Cl. .................. 422/297; 422/292; 422/300; 206/363; 206/370

(58) Field of Classification Search .............. 422/292, 422/294, 297, 300; 206/263, 363, 369, 370
See application file for complete search history.

(56) References Cited

U.S. PATENT DOCUMENTS

| | | |
|---|---|---|
| 3,890,096 A | 6/1975 | Nichol et al. |
| 4,135,868 A | 1/1979 | Schainholz |
| 4,267,939 A | 5/1981 | Perrett et al. |
| 4,327,060 A | 4/1982 | Nissi |
| 4,541,992 A | 9/1985 | Jerge et al. |
| 4,643,303 A | 2/1987 | Arp et al. |
| 4,728,504 A | 3/1988 | Nichols |
| 4,774,063 A | 9/1988 | Runnells |
| 4,798,292 A | 1/1989 | Hauze |
| 4,854,475 A | 8/1989 | Riihimaki et al. |
| 4,886,165 A | 12/1989 | Annett |
| 4,915,913 A | 4/1990 | Williams et al. |
| 4,959,199 A | 9/1990 | Brewer |
| 5,004,418 A | 4/1991 | Porteous |
| 5,080,874 A | 1/1992 | Nichols |
| 5,084,251 A | 1/1992 | Thomas |
| 5,098,676 A | 3/1992 | Brooks, Jr. |
| 5,183,643 A | 2/1993 | Nichols |
| 5,207,325 A | 5/1993 | Kennedy |
| 5,211,915 A | 5/1993 | Monch |
| 5,215,726 A | 6/1993 | Kudla et al. |
| 5,271,893 A | 12/1993 | Newman |
| 5,279,800 A | 1/1994 | Berry, Jr. |
| 5,284,632 A | 2/1994 | Kudla et al. |
| 5,305,876 A | 4/1994 | Brigham |
| 5,340,551 A | 8/1994 | Berry, Jr. |
| 5,346,075 A | 9/1994 | Nichols et al. |
| 5,346,677 A | 9/1994 | Risk |
| 5,384,103 A | 1/1995 | Miller |
| 5,424,048 A | 6/1995 | Riley |
| 5,433,929 A | 7/1995 | Riihimaki et al. |
| 5,441,707 A | 8/1995 | Lewis et al. |
| 5,492,671 A | 2/1996 | Krafft |
| 5,525,314 A | 6/1996 | Hurson |
| 5,630,507 A | 5/1997 | Baker |

(Continued)

FOREIGN PATENT DOCUMENTS

WO        WO9730737 A1    8/1997

Primary Examiner—Sean E Conley
(74) Attorney, Agent, or Firm—Guerry L. Grune; ePatent Manager (57) ABSTRACT

The invention relates to product, method and system for materials handling apparatus and more particularly to an integrated design of a vessel for combining sterilization, storage, transport and presentment of dental or surgical instruments or implants using a uniquely designed sterilization tray. Fabrication of the tray and the number of parts required can be greatly cost reduced, due to the simplicity of the design.

9 Claims, 8 Drawing Sheets

U.S. PATENT DOCUMENTS

| | | |
|---|---|---|
| 5,725,097 A | 3/1998 | Bettenhausen et al. |
| 5,759,502 A | 6/1998 | Spencer et al. |
| 5,843,387 A | 12/1998 | Dane et al. |
| 5,913,422 A | 6/1999 | Cote et al. |
| 5,938,063 A | 8/1999 | Hoftman |
| 6,050,104 A * | 4/2000 | Corona ...................... 62/457.4 |
| 6,116,452 A | 9/2000 | Hamel et al. |
| D441,457 S | 5/2001 | Neiner et al. |
| 6,634,499 B2 | 10/2003 | Allen et al. |
| 6,759,017 B2 | 7/2004 | Wu et al. |
| 2003/0029474 A1* | 2/2003 | Gibbs et al. .................... 134/1 |
| 2003/0211023 A1* | 11/2003 | Wu et al. .................... 422/297 |

* cited by examiner

STERILIZATION TRAY WITH BASE AND ELASTOMERIC LID

FIELD OF INVENTION

This invention relates to a materials handling apparatus and more particularly to an integrated design of an assembly for facilitating sterilization, storage, transport and presentment of dental or surgical instruments or implant using a uniquely designed sterilization tray.

BACKGROUND OF THE INVENTION

The use of a sterilization tray, container or cassette for sterilization and storage of medical and/or dental instruments or implants is well known. The sterilization device usually consists of a tray, or base, and a cover. Both the tray and cover have vertical or near vertical walls on all sides which allow for the tray and cover to mate forming an enclosed container. It is common for the tray and cover to be perforated to allow sterilization and high temperature gasses and fluids to enter and exit the container. The tray and cover may be sheet metal or rigid thermoplastic.

The containers or enclosures are of various height, width and depth depending on the type and size of instruments to be sterilized, autoclaved, or lyophilized. The tray and cover may be separate components or removeably hinged to each other and may contain one or more latching devices to secure the cover to the tray. In some designs the latches form handles for movement of the enclosure as a single unit. Most of the units are stackable, whether for autoclaving or for storage.

The instruments are generally held within the sterilization tray in spaced relation to each other and within the walls of the tray. The means of holding the instruments with the tray includes a variety of instrument supports, clamping members, elastomeric forms, elastomeric mats and other instrument retaining means. Instrument support may be horizontal in a longitudinal direction, compartmentalized or vertically stacked. Tray and cover designs include selectively located holes or slots used as locating tabs for small barriers or walls for customizing component trays within the tray or cover. In previous designs the finger mat, instrument support bracket, clamp, compartments and customizable compartment sides are separate components that require assembly, securing and risk of component loss.

Various other approaches may employ an upright flexible silicone bracket with trunnion and pivoting lid requiring a minimum of a four part assembly or a cylinder containing internal and external threads that must be unthreaded to expose the instruments for use. All of these sterilization tray configurations require the practitioner to use a time-consuming step of removing a separate lid, unclipping or disengaging, minimally, a two-piece assembly. The latching apparatus is also prone to damage with repeated use. With medical and dental practitioners seeing up to 30 patients in one day, many sterilization cycles of the autoclave are required.

Notwithstanding advances made in the prior art, the manufacture of two part instrument sterilization trays from sheet metal remains costly, particularly in higher volumes. Two part sheet metal sterilization tray and lid designs have remained relatively cumbersome and require a hinge or clip element and a latching mechanism that fails frequently with repeated autoclaving.

An advantage of the present invention is provision of an elastomeric lid which acts as both a flexible instrument retention device and a stackable lid for the sterilization tray as a single element. This elastomeric lid, rigid tray design provides a manufacturing cost advantage by providing fewer parts required for assembly. A desired method of manufacture is to directly injection mold the elastomeric lid with an integrated instrument retention member and instrument retention brackets onto the rigid metal or plastic base, thereby further reducing manufacturing costs. The elastomeric lid may also incorporate lid side instrument retention brackets.

DESCRIPTION OF PRIOR ART

U.S. Pat. No. 6,116,452 to Hamel, et. al. and assigned to Synthes, describes a covered tray system comprising: a case, a base, at least one wall, and a top edge which forms an opening for the case and a lid for covering the case opening. A pair of rotatable handles mounted to the wall having a rotation axis being rotatable, from a non-lid-securing position to a lid-securing position wherein the lid cannot be removed without rotating the handles. Novelty of invention is the use of bail like handles to fit in recesses provided for in the cover of the tray.

U.S. Pat. No. 5,279,800 to Berry Jr., and assigned to C/T Medical Systems, Ltd, Inc., refers to an autoclavable cassette for the receipt and storage of dental and surgical instruments comprising a tray, a base, sidewalls, end walls which define an open interior space, rack slots and a plurality of mat slots, a lid for attachment to the tray. A lift-out instrument rack for receipt of a plurality of instruments is located in the base and a snap-in finger mat may be inserted into a base including a tab at one end and a spring clip at the opposite end. The cassette base slots are arranged to receive many different customizable inserts for a holding a variety of instruments.

U.S. Pat. No. 5,938,063 to Hoftman, and unassigned, describes a box with a top, a bottom, a hinge and latch arrangement in the sidewalls such that when the halves are in a closed position the floors of the top and bottom have a closed depth of about more than about 10 mm. The sidewall edges securely enclose contents of the box when the box is in the closed position and the latches secured. This invention relates to securing an autoclavable box making it difficult to open in order to protect from accidental exposure to surgical blades and scalpels.

U.S. Pat. No. 4,541,992 to Jerge, et. al., and assigned to Hu-Friedy Manufacturing Co., describes a sterilizable instrument cassette formed of heat resistant plastic perforated with a plurality of openings, a base, cover, and customizable instrument compartment rails fastened to the cover and tray. The tray is stackable with other trays and has a hinge and latching mechanism.

U.S. Pat. No. 4,854,475 to Riihimaki, et. al., and assigned to Hu-Friedy Manufacturing Co., describes a cassette comprising a tray, cover, a hinge including two J-shaped hinges located on the tray and on the cover and a snap latch for securing the cover to the tray. The J-shaped hinges allow for complete separation of the two components.

U.S. Pat. No. 5,346,677 to Risk, and unassigned, describes a cassette for holding and sterilizing dental instruments with a tray, cover, hinges, instrument positioning racks in the tray and the cover, an instrument retaining feature that comprising a pivotable retaining bar. This invention relates to a resilient roller that is compressed between the cover and the tray that applies conformable pressure to the instruments thereby holding them in a desired position.

U.S. Pat. No. 5,433,929 to Riihimaki, et. al., and assigned to Hu-Friedy Manufacturing Co., describes an instrument sterilization and storage cassette which claims priority to U.S. Pat. No. 5,215,726 with a resilient crosspiece used for securing the instruments in position, when the cassette is closed, that is hinged to the tray and the cover and perpendicularly folded over the instrument shafts.

U.S. Pat. No. 6,634,499 to Allen, et. al., and assigned to Paragon Medical, describes a tray for medical instruments that has customizable inserts that fit into features in the tray and allows for frictional securing of medical instruments for sterilization. Trunions are preferably made of a silicon composition.

U.S. Pat. No. 5,630,507 to Baker, and assigned to Carr Metal Products Inc, describes a cantilevered latch system for securing a cover to a box for medical use.

U.S. Pat. No. 5,340,551 to Berry Jr, and assigned to C/T Medical Systems, Ltd, Inc., describes an autoclavable cassette with a spring clip latching system which is has an aperture that is pushed around a latching pin to secure the cover to the tray. It is customizable with finger mats, supports and individual cassettes.

U.S. Pat. No. 5,215,726 to Kudla, et. al., and assigned to Hu-Friedy Manufacturing Co., describes a customizable instrument sterilization tray with a clamping mechanism wherein the tray and the cover are not hinged to each other.

U.S. Pat. No. 5,913,422 to Cote, et. al., and assigned to Poly Vac, Inc., describes an improvement which comprises a retention pad formed of a resiliently deformable material located in fixed position within a sterilization cassette that is configured to releasable grip surgical instruments.

U.S. Pat. No. 5,725,097 to Bettenhausen, et. al., and assigned to Sterilization Cassette Systems, Inc., describes a sterile wrap used to enclose the sterilization cassette to maintain sterility of the instruments.

U.S. Pat. No. 5,284,632 to Kudla, et. al., and assigned to Hu-Friedy Manufacturing Co., describes a tray base and cover that have a rotatable resilient bar that is used to clamp over the instruments to maintain the instruments in a fixed position.

U.S. Pat. No. 3,890,096 to Nichol, et. al., and unassigned, describes a stackable tray for holding dental instruments while they are sterilized in an autoclave.

U.S. Pat. No. 4,541,992 to Jerge, et. al., and assigned to Hu-Friedy Manufacturing Co., describes a tray, cover and instrument holder formed of sterilization heat resistant plastic wherein the cover and the tray are joined by features on the cover and tray.

U.S. Pat. No. 4,643,303 to Ap, et. al., and assigned to Micromedics Inc., describes an autoclavable surgical tray storage and transporting assembly with a removable wire basket and at least one flat plastic reformable sheet with holes and recesses to accept surgical instruments.

U.S. Pat. No. 4,774,063 to Runnels, Robert, and assigned to MDT Biologic Co., describes a tray and cover with a Morton-like latching mechanism.

U.S. Pat. No. 4,959,199 to Brewer, Charles, and unassigned, describes an autoclavable cassette wherein the cassette has holders for dental instruments attached to the base and the cover and a clamping means incorporated into the cover or the holders.

U.S. Pat. No. 5,004,418 to Porteous, Paul, and unassigned, describes a dental instrument mat with a means for aligning dental instruments and a removable retaning means located in both the cover and the tray which exert a force on the instruments causing them to be held in position.

U.S. Pat. No. 5,084,251 to Thomas, Akatheputhethu, and unassigned, describes an instrument sterilization cassette with a means of blocking off portions of the spaces allowable for the entry and egress of sterilizing disinfectant.

U.S. Pat. No. 5,098,676 to Brooks Jr., John, and unassigned, describes a sterilization tray mat made of silicon rubber and sized to fit a tray and cover having projections spaced at predetermined locations, said mats being removable.

U.S. Pat. No. 4,267,939 to Perrett, et. al., and assigned to Synthes, describes a sterilization cassette wherein the latches are integral to the handles. When the latches are securing the cover, they form handles for portability for the tray.

U.S. Pat. No. 4,728,504 to Nichol, Robert, and unassigned, describes a stackable configuration of sterilization trays that incorporate a sloped inner base surface for the collection and disposal of residual sterilization fluids or gasses.

U.S. Pat. No. 4,798,292 to Hauze, Dennis, and assigned to Biomedical Laser Industries, describes a sterilization container wherein the cover may be inverted to provide a second tray and instruments are held in place by rods inserted through prelocated holes in the trays.

U.S. Pat. No. 4,915,913 to Williams, et. al., and assigned to Genesis Medical Corp., describes an improved latching mechanism for a sterilization device.

U.S. Pat. No. 5,080,874 to Nichols, Robert, and unassigned, describes a stackable system of sterilization trays wherein the drainage ports for sterilization fluid for the uppermost tray is offset from the input ports of the lower tray.

U.S. Pat. No. 5,183,643 to Nichols, Robert, and unassigned, describes a stackable system of sterilization trays wherein the drainage ports for sterilization fluid for the uppermost tray is offset from the input ports of the lower tray and a filtration device is put in place to enable the passage of gasses and fluids, but not the passing of contaminants.

U.S. Pat. No. 5,207,325 to Kennedy, Patricia, and unassigned, describes a high temperature thermoplastic sterilization tray with apertures for constructing compartments to create desired compartments for specific surgical instruments.

U.S. Pat. No. 5,211,915 to Monch, Harry, and assigned to Richard Wolf GmbH, describes a receptacle for containing medical instruments wherein there is a removable mat with spikes projecting upwardly from the base for supporting instruments and a mat removably attached to the underside of the cover to retain said instruments in the base when the cover is latched to the base.

U.S. Pat. No. 5,346,075 to Nichols, et. al., and assigned to Johnson & Johnson Medical Products, describes customizable sterilization apparatus wherein inserts may be removably attached to selected apertures in the tray and cover.

U.S. Pat. No. 5,384,103 to Miller, Curtis, and assigned to Micromedics, Inc., describes a customizable sterilization tray wherein compartments, in successive transitions, become smaller to compartmentalize various size medical instruments.

U.S. Pat. No. 5,424,048 to Riley, Edward, and assigned to Riley Medical, Inc., describes a rigid case with a plurality of holes in the sides wherein the instruments within may be placed a desired location within the case.

U.S. Pat. No. 5,441,707 to Lewis, et. al., and assigned to Paragon Medical, Inc., describes a sterilization tray with an internal ridge for supporting the insertion of instrumentation trays constructed with curved edges that rest on the ridge surfaces.

U.S. Pat. No. 5,525,314 to Hurson, Steven, and assigned to Bausch & Lomb, Inc., describes a sterilization tray wherein the instruments are placed in a series of grommets and held basically in a vertical direction wherein the grommet mat is a removable mat.

U.S. Pat. No. 4,886,165 to Annett, Leland, and assigned to Medical Concepts Development, Inc., describes a covered disposable box useful in accounting for surgical devices.

U.S. Pat. No. 4,327,060 to Nissi, Alessandro, and unassigned, describes a cylinder with spaces for holding dental instruments in an upright position and where the cylinder has internal and external threads to allow for threadedly joining the upper and lower portions of the cylinder to form a airtight container.

U.S. Pat. No. 4,135,868 to Schainholz, Herbert, and unassigned, describes a sterilization tray with a circularly perforated insert to allow for customization if instrument supports.

U.S. Pat. No. 6,759,017 to Wu, et. al., and assigned to Ethicon Inc., describes a sterilization container stacking separator that allows for diffusion of sterilization fluids.

U.S. Pat. No. 5,843,387 to Dane, et. al., and assigned to Poly Vac Inc., describes a sterilization tray assembly with a series of deformable and resilient locking features for the insertion of medical instruments.

U.S. Pat. No. 5,759,502 to Spencer, et. al., and assigned to Sterilization Cassette Systems Inc., describes an instrument cassette wherein the instrument holding supports are fastened with a nut and bolt to the tray.

U.S. Pat. No. 5,492,671 to Krafft, Petrus and assigned to Zimmer Inc., describes a steam sterilization case and a series of customizable inserts for holding various types and sizes of medical instruments.

U.S. Pat. No. 5,305,876 to Brigham, Susan and unassigned, describes a sterilization cassette used for orthodontia and various components wherein the cassette compartments may be identified per patient.

U.S. Pat. No. 5,271,893 to Newman, Duncan, and unassigned, describes a system of steam sterilizing articles wherein the system controls a jet of high temperature sterilizing fluid.

U.S. Pat. No. USD441,457 to Neiner, et. al., and assigned to Hu-Friedly Manufacturing Co., describes a hinged design for a sterilization cassette. WIPO Publication WO9730737A1 to Lackey, et. al., and assigned to Smith & Nephew Inc., describes a method of supplying a plurality of sterilized surgical instruments for specific use in orthopedic surgery.

Therefore there exists a need for a sterilization enclosure cover component that provides an elastomeric fit which encompasses a tray to form a single device for the sterilization and transportation of medical and dental instruments or implants.

SUMMARY OF THE INVENTION

The present invention provides a foraminous sterilization tray having a rigid base, side walls extending from the perimeter of the base in a vertical or near vertical angle and a foraminous flexible elastomeric lid that is easily stretched on and off the rigid base and side walls enclosing the base and side walls into a single enclosure.

Another object of this invention is to provide an integral, single component design which incorporates supports for instruments as longitudinal supports or finger mats in the cover for insertion into the tray.

It is also an object of this invention to promote stacking of the sterilization enclosures for storage or transportation.

It is also an object of this invention to eliminate the addition of a hinge or mechanical latching mechanism for securing the cover to the tray.

It is also an object of this invention to provide one piece molded, securable instrument supports in the cover cavity to provide for additional instrumentation sterilization.

It is also an object of this invention to provide a comfortable gripping surface on the outside of the sterilization enclosure.

It is also an object of this invention to provide integrated instrument retention members for securing instruments into the instrument retention brackets in the tray.

It is also an object of this invention to enable a color-coded elastomeric lid to allow rapid identification of the enclosed instruments.

It is also an object of this invention to overmold a rigid high temperature elastomer base with a flexible silicon rubber overmold to produce a single component enclosure.

An additional object of the present invention includes providing a tray and cover assembly with a single cavity mold, such that the tray and cover with the associated finger mat or other instrument holding means can be completely produced in a single operation. This single operation may be with the use of the same materials for both the tray and cover (single port for filling) or with two or more separate materials (two or more ports for filling), where the tray would be rigid or semi-rigid and the cover would be more flexible and stretchable.

Further objects and advantages will become apparent from consideration of the ensuing description and drawings.

DETAILED DESCRIPTION OF THE INVENTION

For the purpose of representing the principles of the invention, reference will now be made to the drawings and specific language will be used to describe the same. It will nevertheless be understood that no limitation of the scope of the invention is thereby intended, such alterations and further modifications in the illustrated device and such further application of the principles of the invention as illustrated therein being contemplated as would normally occur to one skilled in the art are included as part of the present invention.

Figure 1:
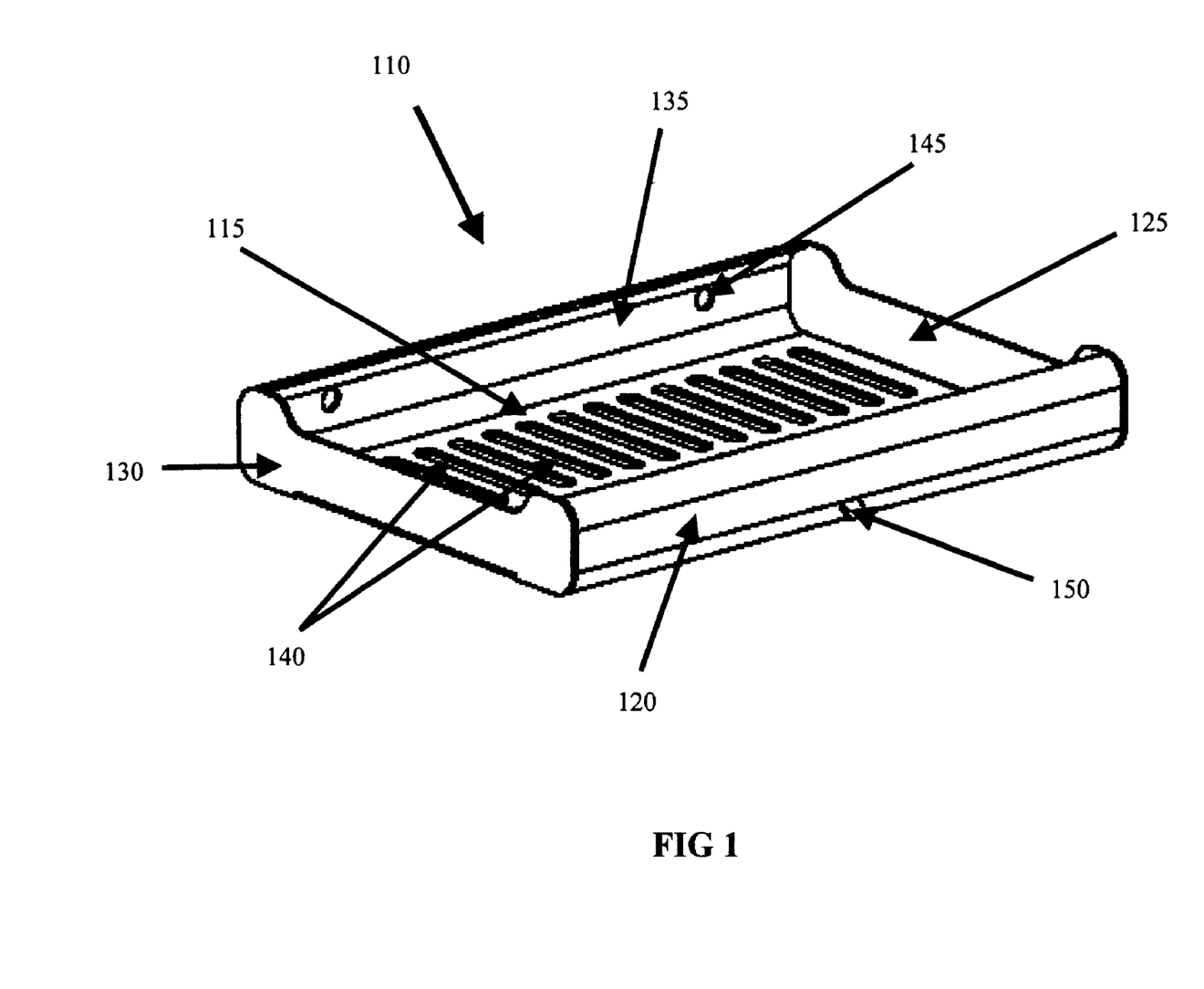
FIG. 1 illustrates a rigid metal or plastic tray only.

FIG. 1 shows the tray [110] component with a generally rectangular base [115], attached to a front wall [120], a right wall [125], a left wall [130] and a rear wall [135] that contact each other and are nearly perpendicular to the base [115] and to each other. The base [115] has multiple apertures [140] which may be of various shapes, sizes and locations. The rear wall [135] has one or more tray orientation perforations [145] and the front wall [120] has a wall hook [150].

Figure 1A:
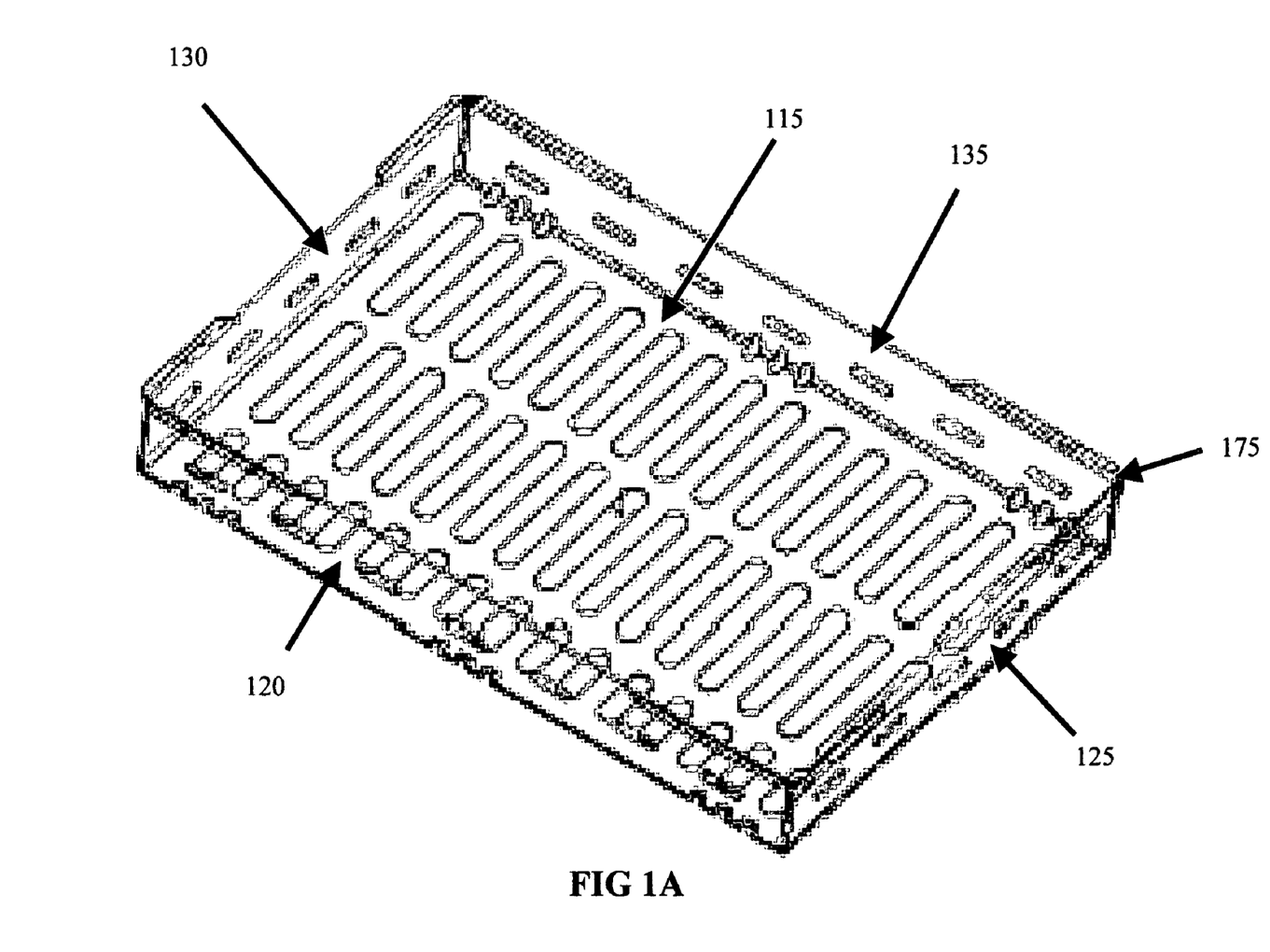
FIG. 1A illustrates a rigid or semi-rigid tray with rounded edges and associated insulation along those edges to facilitate the attachment and removal of an elastomeric lid.

FIG. 1A identifies sidewall lip features [175] molded or added on to four corners at the intersection of the wall [120, 125, 130, 135] either in contact with the base [115] or not in contact with the base.

Figure 2:
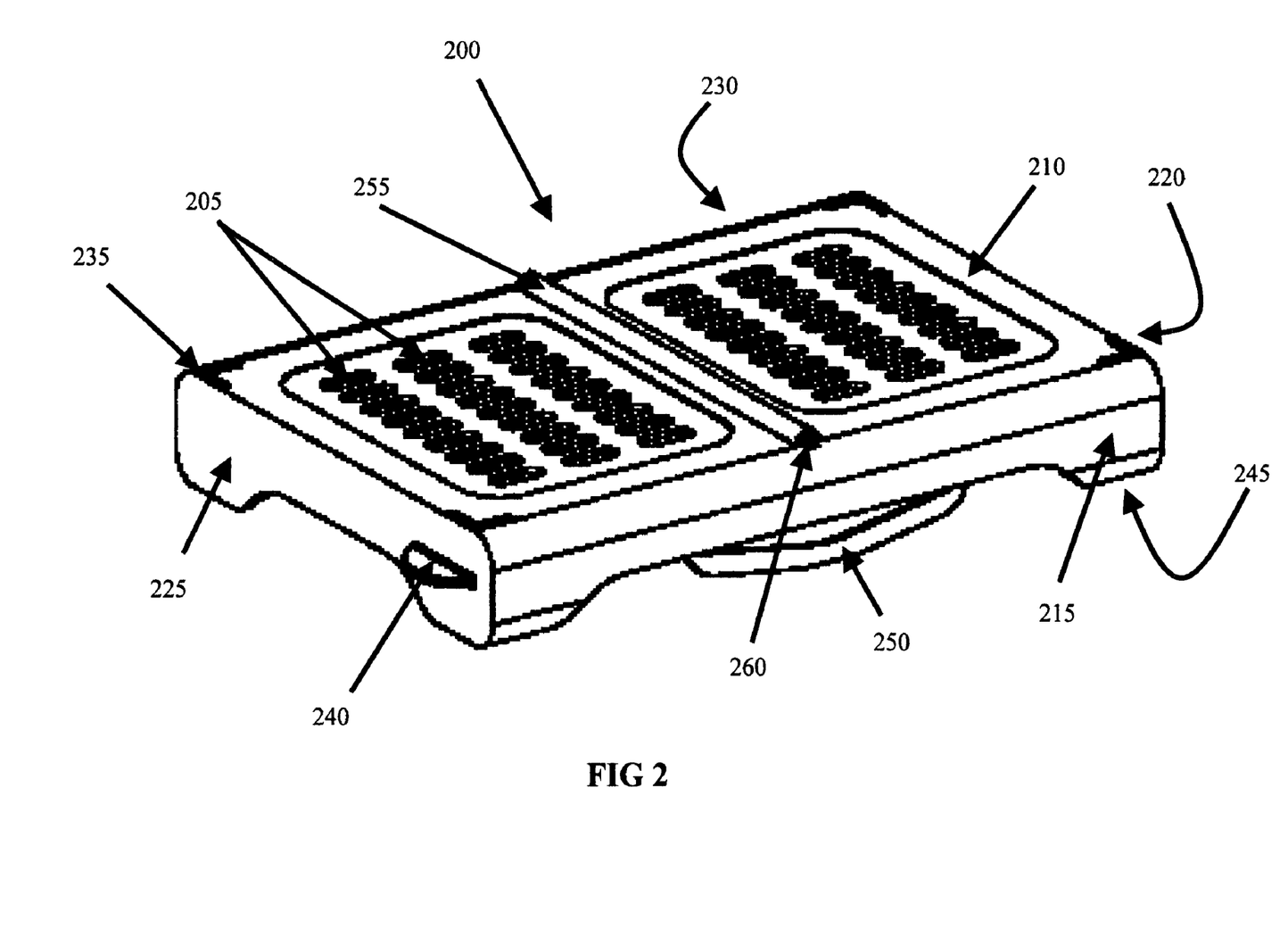
FIG. 2 illustrates the elastomeric lid.

FIG. 2 illustrates the flexible elastomeric lid [200] preferably produced with silicone rubber or other high heat resistant elastomers, with a multiplicity of upper apertures [205] through the lid top [210] which is joined perpendicularly to the front flange [215], the right flange [220], the left flange [225] and the rear flange [230]. The surface of the lid top [210] contains four stacking corner tabs [235]. Multiple lid pull tabs [240] protrude from the right flange [220] and the left flange [225]. Cupped corners [245] are formed such that the front flange [215], right flange [220], left flange [225] and rear flange [230] turn down to form the curvilinear cupped corners [245]. One or more attaching loop(s) [250] is part of the front flange [215]. The rear flange [230] also contains cupped corners [245] at each end. Additionally, a hollow tube [255] may be added to the lid top [210] for the insertion of an optional rigid rod [260] for structural integrity during stacking.

Figure 3:
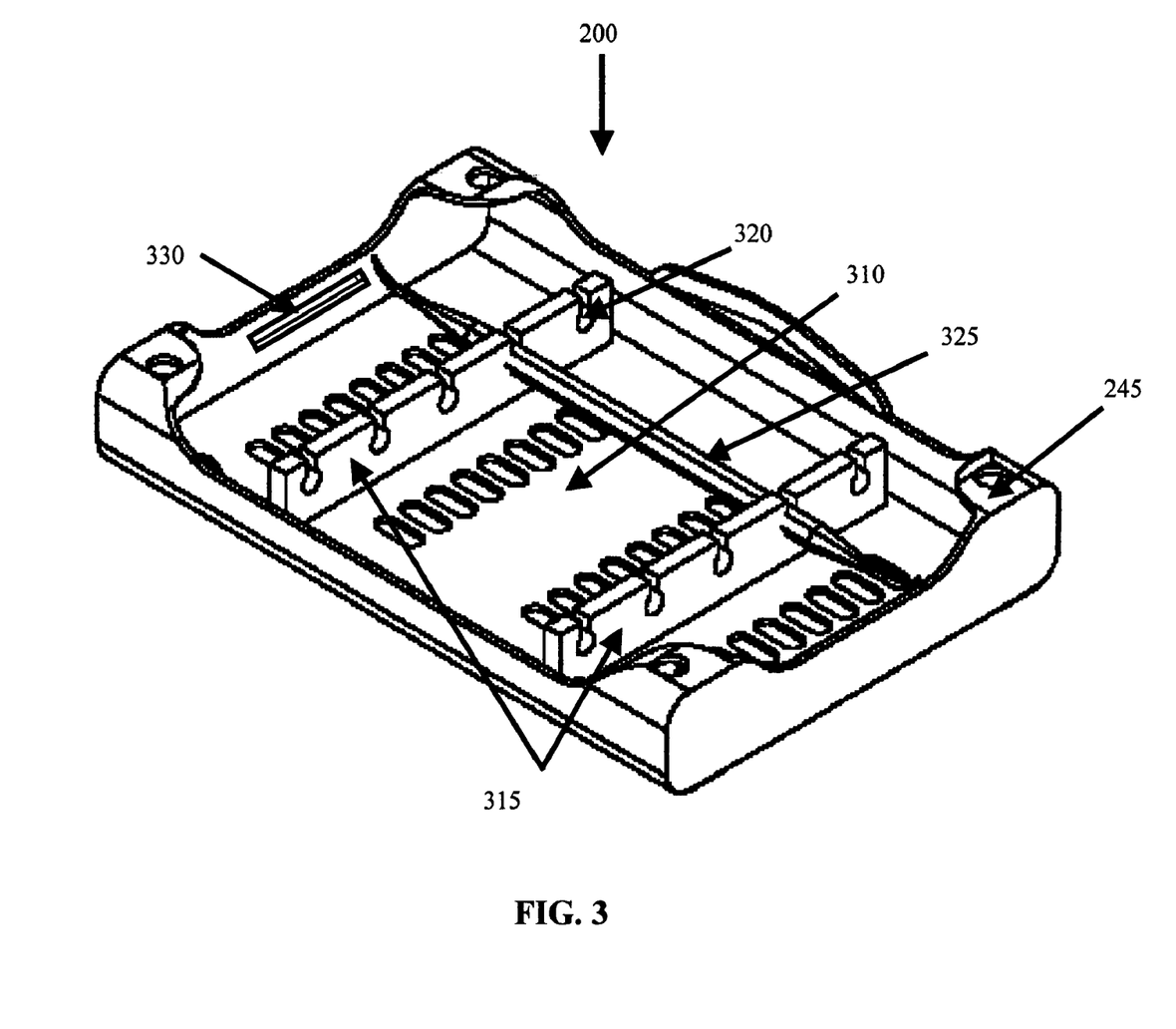
FIG. 3 illustrates the elastomeric lid only with the bottom of the lid facing up.

FIG. 3 provides a pictorial representation of the lid [200] shown upside down with the top lid, inner [310] surface exposed and showing details of the cupped corners [245] and optional instrument locating brackets [315] with securing tabs [320] and surgical or dental instruments [325] placed in the locating brackets [315] and a lid guide notch [330].

Figure 4:
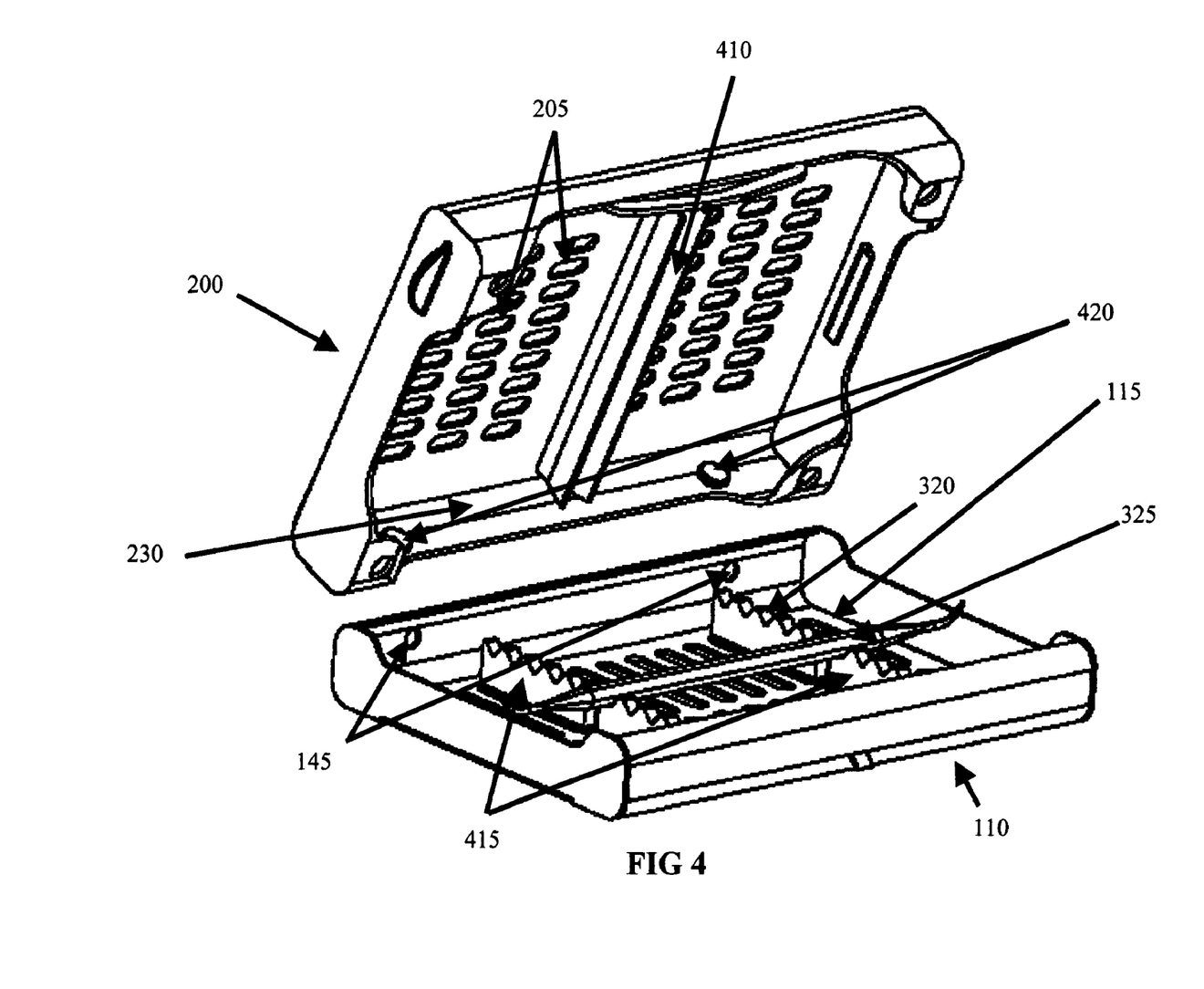
FIG. 4 illustrates the sterilization tray with a rigid metal or plastic tray and an elastomeric lid, shown in the opened position for instrument loading and unloading.

FIG. 4 shows the relationship between the tray [110] and the lid [200]. Within the lid [200] is an optional resilient retention member [410] that may be optionally molded into the lid [200] or as a separate component, assembled through one or several upper apertures [205].

When the lid [200] of the tray [110] is closed the retention member [410] compresses against any medical or dental instruments [325] that may be placed in the tray brackets [415] projecting upwards from the base [115], thereby securing the medical or dental instruments [325] in the desired locations. The tray brackets, [415] may optionally have securing tabs [320]. Orientation nubs [420] are located on the inside surface of the rear flange [230] for insertion into the tray orientation perforations [145].

Figure 5:
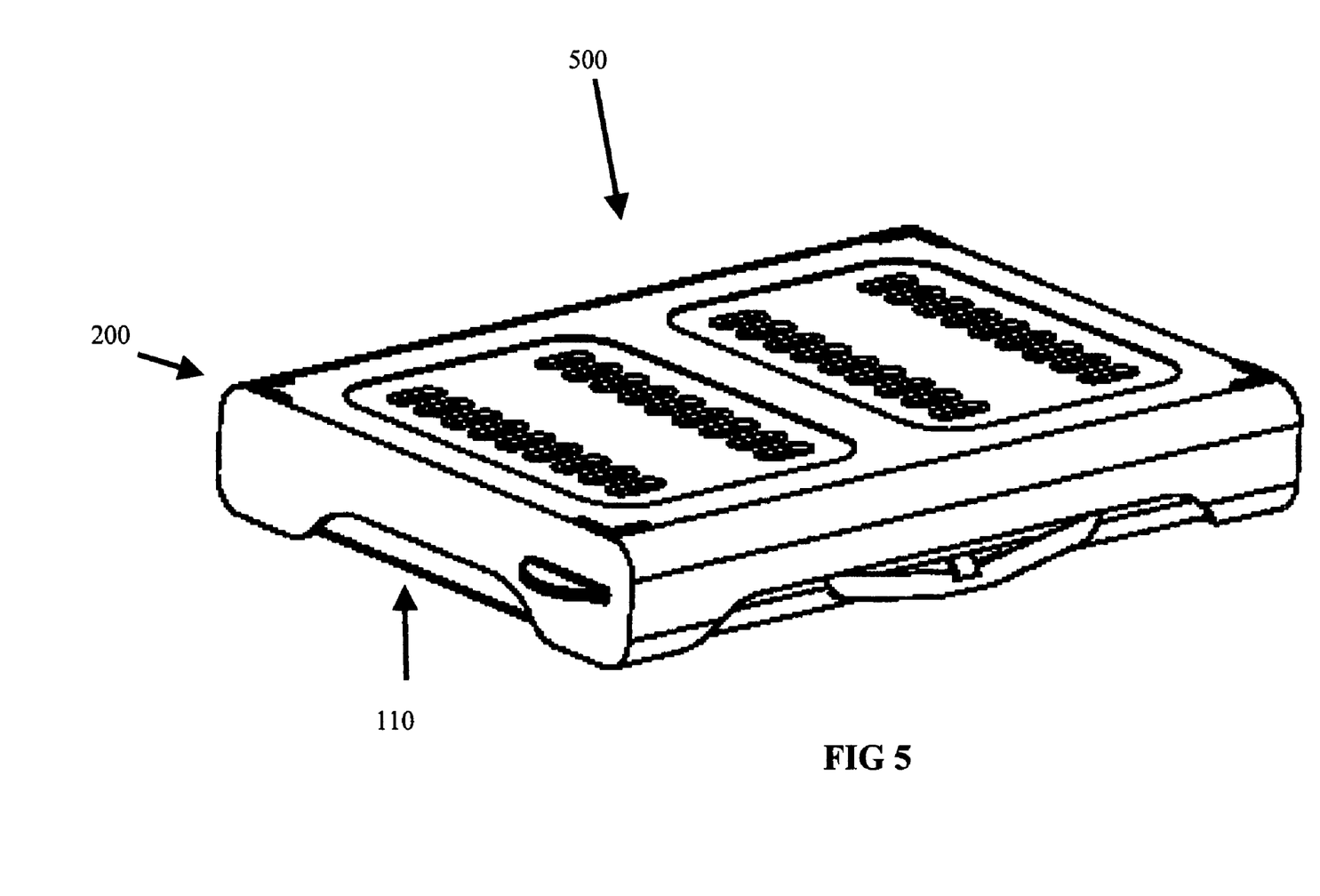
FIG. 5 illustrates the sterilization tray with a rigid metal or plastic tray and elastomeric lid, as shown in the closed position.

FIG. 5 illustrtates the medical or dental sterilization tray assembly [500] in the closed position with an elastomeric lid [200] and rigid tray [110]. Details of the assembly process are noted below:

The lid [200] orients onto the tray [110] by inserting the orientation nubs [420] into the tray orientation perforations [145] and by inserting the cupped corners [245] located on the rear flange [230] around the corners of the rear wall [135]. The lid [200] is then grasped by the cupped corners [245] located on the front flange [215] and rotatably stretched over the front wall [120] corners thereby securing the lid [200] to the tray [110] creating a tray assembly [500]. The attaching loop [250] is then stretched over the wall hook [150] to secure the lid [200] to the tray [110]. Removal of the lid [200] from the tray [110] is accomplished by grasping the pull tabs [240] and rotatably stretching the lid [200] from the front flange [215] toward the rear flange [230] and disassociating the cupped corners [245] from the front wall [120].

Figure 6:
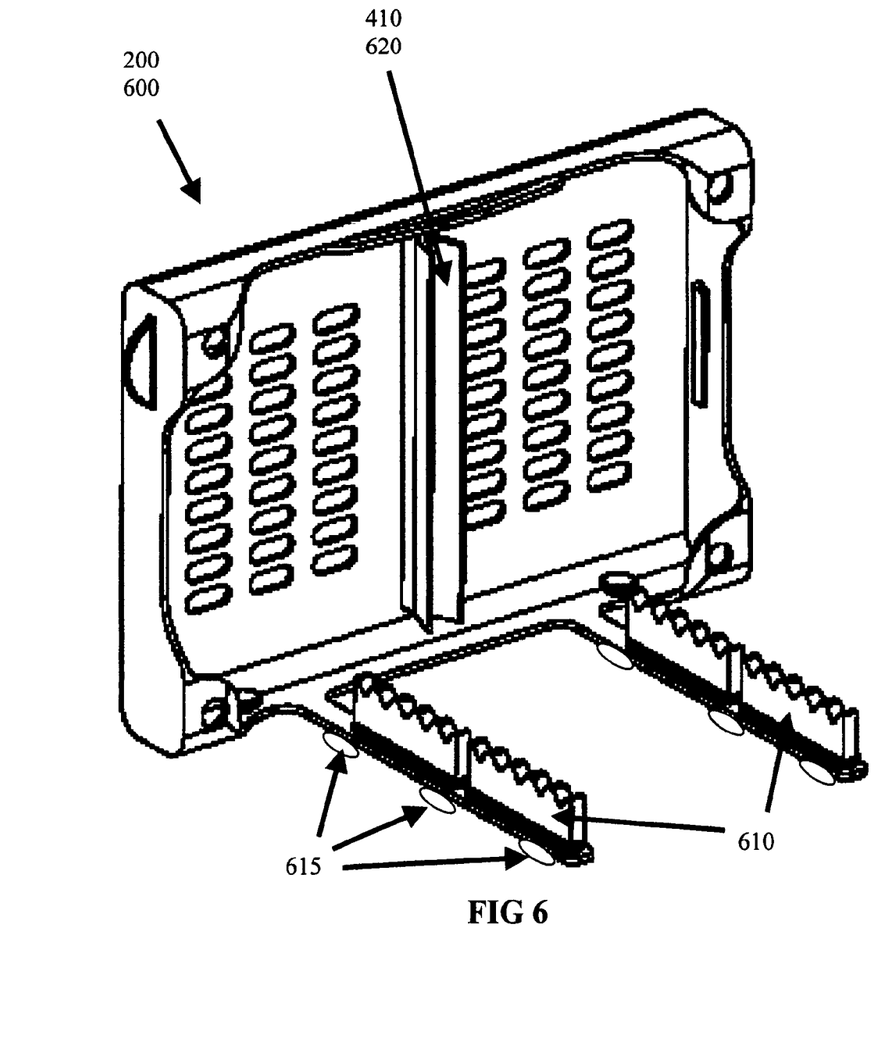
FIG. 6 illustrates the elastomeric lid with integrated instrument retention members, instrument retention brackets and gripping protrusions.

FIG. 6 references an alternative embodiment of an elastomeric lid [200]. This bracket lid [600] embodiment has integral tray instrument retention brackets [610], elastomeric gripping protrusions [615], and an instrument retention bracket [620] similar to the retention member [410].

Figure 7:
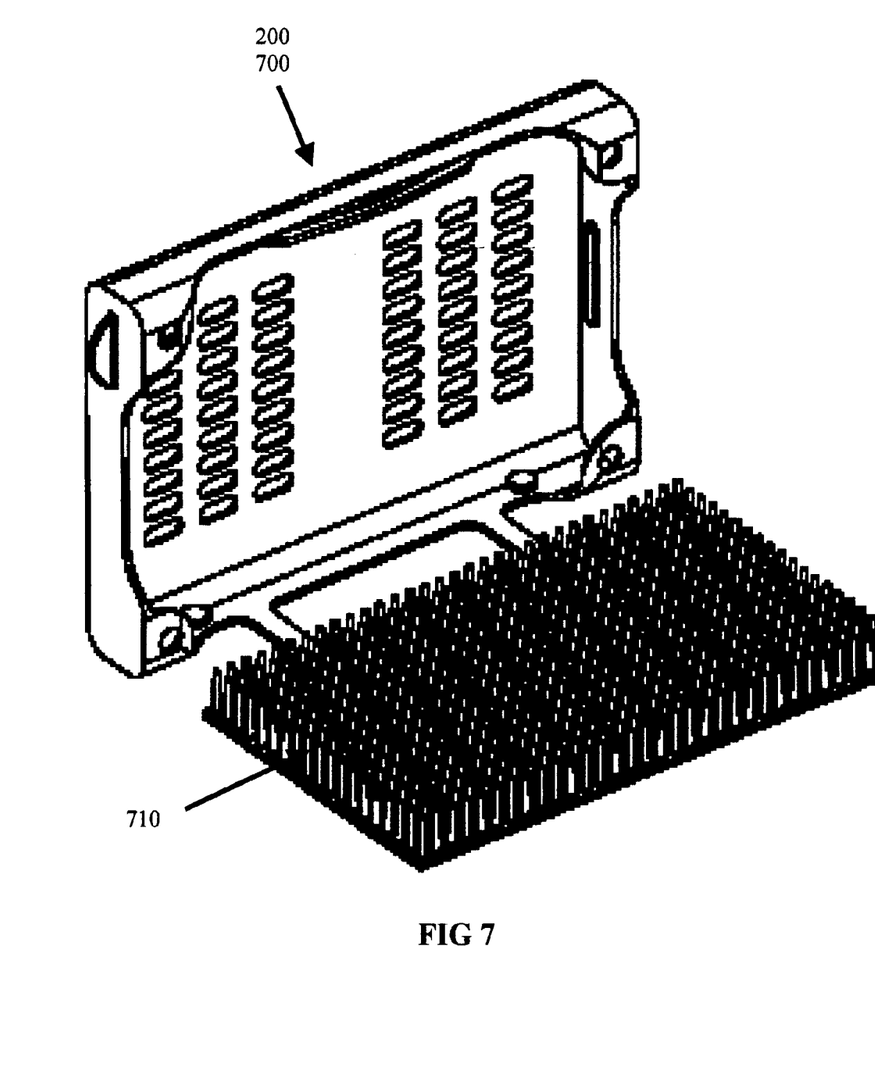
FIG. 7 illustrates the elastomeric lid with an integrated finger mat.

FIG. 7 references an alternative embodiment of an elastomeric lid [200]. This finger mat lid [700] embodiment has an integral finger mat [710]. Another embodiment includes slight separations at each corner of the elastomeric lid [200] or the tray [110].

What is claimed is:

1. A sterilization tray for receipt, storage, and retrieval of dental or medical instruments or implants, said tray comprising; a foraminous rigid or semi-rigid base attached to and bounded by a front wall, a right wall, a left wall and a rear wall, said rear wall having tray orientation perforations and a removable, stretchable, foraminous elastomeric lid, wherein said elastomeric lid includes at least one elastomeric attachable loop that is a portion of said lid and wherein said lid is attached to said rear wall by inserting orientation nubs into said orientation perforations and wherein said lid is also secured to said base by at least one attachable hook on said base, thereby enclosing at least a portion of said front wall, said right wall, said left wall and said rear wall.

2. The elastomeric lid of claim 1, further including at least one lid instrument retention member, fabricated within said elastomeric lid, said base comprising and integrated with at least one tray bracket, said tray bracket protruding upward from said base wherein at least one instrument is laid upon said tray bracket such that application of a downward force is applied on said instruments when said instruments are secured within said at least one lid instrument retention member and said tray bracket.

3. The elastomeric lid of claim 2, wherein said lid is fabricated with said lid instrument retention member as a single element, such that said lid instrument retention member protrudes toward said base while remaining attached to said elastomeric lid.

4. The elastomeric lid of claim 1, wherein said elastomeric lid includes at least one corner attached to said elastomeric lid, wherein said elastomeric lid is fabricated such that one or more of said corner(s) is extended over a lip feature of said front wall, said right wall, said left wall and said rear wall wherein thereby aiding full or partial covering of said base.

5. The elastomeric lid of claim 1, wherein said lid is fabricated using various colors, thereby providing identification for each of said dental or medical instruments or implants.

6. The elastomeric lid of claim 1, wherein said elastomeric lid is fabricated with silicone rubber, urethanes, and or other stretchable materials and or material composites.

7. The sterilization tray of claim 1, wherein said elastomeric lid comprises features sufficient for stacking of multiple sterilization trays.

8. The sterilization tray of claim 1, wherein said tray is fabricated in combination with said elastomeric, stretchable lid such that a combination of said lid and said tray is a single element, and wherein said tray provides at least one instrument retention member protruding upward from said base of said tray.

9. The sterilization tray of claim 1, wherein an instrument retention mat is fabricated in combination with said elastomeric lid providing a single element, and wherein said instrument retention mat includes fingers that protrude upward from said base.

* * * * *